United States Patent
Berlinger et al.

(10) Patent No.: US 9,254,106 B2
(45) Date of Patent: Feb. 9, 2016

(54) METHOD FOR COMPLETING A MEDICAL IMAGE DATA SET

(75) Inventors: Kajetan Berlinger, Munich (DE); Stephan Erbel, Munich (DE)

(73) Assignee: Brainlab AG, Feldkirchen (DE)

( * ) Notice: Subject to any disclaimer, the term of this patent is extended or adjusted under 35 U.S.C. 154(b) by 1109 days.

(21) Appl. No.: 12/760,575

(22) Filed: Apr. 15, 2010

(65) Prior Publication Data

US 2010/0195890 A1 Aug. 5, 2010

Related U.S. Application Data

(60) Provisional application No. 61/169,898, filed on Apr. 16, 2009.

(30) Foreign Application Priority Data

Apr. 15, 2008 (EP) .................................... 09157950

(51) Int. Cl.
*G06K 9/00* (2006.01)
*A61B 6/03* (2006.01)
*A61B 6/00* (2006.01)
*G06T 5/50* (2006.01)
*G06T 11/00* (2006.01)
(Continued)

(52) U.S. Cl.
CPC ............... *A61B 6/032* (2013.01); *A61B 6/5235* (2013.01); *A61B 6/5247* (2013.01); *G06T 5/50* (2013.01); *G06T 11/005* (2013.01); *A61B 5/0064* (2013.01); *A61N 2005/1061* (2013.01); *G06T 2207/10081* (2013.01); *G06T 2211/436* (2013.01)

(58) Field of Classification Search
CPC ................... G06T 7/0012; G06T 2207/10081; G06T 2207/30072; G06T 2207/30004; G06T 7/0024
See application file for complete search history.

(56) References Cited

U.S. PATENT DOCUMENTS 6,873,867 B2   3/2005   Vilsmeier
6,915,005 B1 *  7/2005   Ruchala ................... A61B 6/08
                                                          382/131

(Continued)

FOREIGN PATENT DOCUMENTS

EP     1 142 536      10/2001
WO    03/105069      12/2003

OTHER PUBLICATIONS

Ruchala et al., "Methods for improving limited field-of-view radiotherapy reconstructions using imperfect a priori images", Medical Physics, AIP, vol. 29, No. 11, Nov. 2002.

*Primary Examiner* — Fonya Long
*Assistant Examiner* — Kristine Rapillo
(74) *Attorney, Agent, or Firm* — Tucker Ellis, LLP; Patrick Clunk; Michael Hudzinski

(57) ABSTRACT

The present invention relates to a method for generating a complete medical image data set from an incomplete image data set, comprising the method steps of: providing a first image data set which represents an image of a first region of a body, including at least a part of the surface of the body, at a first point in time; providing a second, incomplete image data set which represents an image of a second region of the body at a second point in time, wherein the first region and the second region overlap; providing a third data set which represents the contour of the body in the form of points on the surface of the body, substantially at the second point in time; adapting the first image data set to the second image data set by taking into account the third data set; and accepting the adapted first image data set as a complete image data set.

15 Claims, 2 Drawing Sheets

(51) Int. Cl.
*A61B 5/00* (2006.01)
*A61N 5/10* (2006.01)

(56) References Cited

U.S. PATENT DOCUMENTS

| | | | |
|---|---|---|---|
| 7,623,709 B2 * | 11/2009 | Gering | G06T 7/0081 |
| | | | 382/173 |
| 2002/0002330 A1 | 1/2002 | Vilsmeier | |
| 2005/0143645 A1 | 6/2005 | Vilsmeier | |
| 2007/0036410 A1 * | 2/2007 | Ida | G06T 7/0024 |
| | | | 382/128 |
| 2007/0195923 A1 | 8/2007 | Netsch et al. | |
| 2009/0028403 A1 * | 1/2009 | Bar-Aviv | G06F 19/321 |
| | | | 382/128 |
| 2010/0172567 A1 * | 7/2010 | Prokoski | A61B 5/0064 |
| | | | 382/132 |

* cited by examiner

METHOD FOR COMPLETING A MEDICAL IMAGE DATA SET

RELATED APPLICATION DATA

This application claims the priority of U.S. Provisional Application No. 61/169,898, filed on Apr. 16, 2009, which is hereby incorporated in its entirety by reference.

FIELD OF THE INVENTION

The present invention relates to a method and device for generating a complete medical image data set from an incomplete image data set.

BACKGROUND OF THE INVENTION

In the field of medicine, it is often necessary to have an exact image of a body in order for example to plan and/or perform surgery or an irradiation treatment, wherein it is necessary to obtain the image as immediately before the irradiation and/or treatment as possible, since a body can significantly change even within short periods of time. Such images are predominantly obtained by means of cone beam computed tomographs (CBCT), since they represent relatively simple apparatuses for 3D imaging and only require a little time to prepare the image. However, because of the cone beam, they have the disadvantage of exhibiting only a limited detection range which often does not include the entire relevant region of the body. Moreover, their spatial resolution and dynamic range are lower than with fan beam computed tomographs (CT) or magnetic resonance tomographs (MRT).

In order to avoid this disadvantage, the U.S. Pat. No. 6,915,005 B1 suggests: preparing a CT image, chronologically before the CBCT image, which captures a larger region of the body than the CBCT image; aligning the CT image onto the CBCT image; converting the aligned CT image into a sinogram; and supplementing regions of the sinogram of the CBCT image outside the detection range of the CBCT image from the sinogram of the aligned CT image.

SUMMARY OF THE INVENTION

It is the object of the present invention to improve the method and device such as are known from the prior art, to the effect that it is possible to generate the complete medical image data set more quickly, and to the effect that the completed medical image data set more precisely matches the current state of the body.

This object is solved by a method for generating a complete medical image data set from an incomplete image data set, comprising the method steps of: providing a first image data set which represents an image of a first region of a body, including at least a part of the surface of the body, at a first point in time; providing a second, incomplete image data set which represents an image of a second region of the body at a second point in time, wherein the first region and the second region overlap; providing a third data set which represents the contour of the body in the form of points on the surface of the body, substantially at the second point in time; adapting the first image data set to the second image data set by taking into account the third data set; and accepting the adapted first image data set as a complete image data set, and by a computer program which, when it is run on a computational unit, performs the method steps according to the aforementioned method, and by a device for generating a complete medical image data set from an incomplete image data set, comprising: an interface for receiving a first image data set which represents an image of a first region of a body, including at least a part of the surface of the body, at a first point in time; a device for generating a second, incomplete image data set which represents an image of a second region of the body at a second point in time, wherein the first region and the second region overlap; a device for generating a third data set which represents the contour of the body in the form of points on the surface of the body, substantially at the second point in time; and a computational unit which is configured to adapt the first image data set to the second image data set by taking into account the third data set, and to accept the adapted first image data set as a complete image data set. Advantageous embodiments can be gathered from the dependent patent claims.

In accordance with the method in accordance with the invention for generating a complete medical image data set from an incomplete image data set, a first image data set is provided which represents an image of a first region of a body, including at least a part of the surface of the body, at a first point in time. The first image data set is preferably complete, but may no longer be up-to-date at the time of the treatment. A second, incomplete image data set is also provided which represents an image of a second region of the body at a second point in time, wherein the first region and the second region overlap. The second point in time is later than the first point in time. A third data set is also provided which represents the contour of the body in the form of points on the surface of the body, substantially at the second point in time.

The wording "substantially at the second point in time" means that the point in time at which the third data set is obtained does not deviate at all or only slightly deviates from the second point in time. The difference in time between generating the third data set and the second point in time is significantly smaller, for example at most a twentieth, preferably at most a hundredth, of the difference in time between the first point in time and the second point in time. The second image data set and the third data set are preferably prepared simultaneously or within a few minutes, while the period of time between the first point in time and the second point in time can be a number of hours, days or even weeks.

In accordance with the present method, the first image data set is also adapted to the second image data set by taking into account the third data set. This means that the first image data set is matched as well as possible to the second image data set, for example by shifting and/or rotating the first image data set with respect to the second image data set and/or any distortion of the first image data set. Methods for adapting one image data set to another image data set are known from the prior art, for example by the names "image matching" or "image fusion". Finally, the adapted first image data set is accepted as a complete medical image data set.

Where data, regions, ranges or images are "provided", this means that they are ready for use by the method in accordance with the invention. The data, regions, ranges or images can achieve this state of being "provided" by for example being detected or captured (for example by analysis apparatuses) or by being input (for example via interfaces). The data can also have this state by being stored in a memory (for example a ROM, CD and/or hard drive) and thus ready for use within the framework of the method in accordance with the invention. The data, regions, ranges or images can also be determined, in particular calculated, in a method step before being provided, in particular before being stored.

In accordance with the method in accordance with the invention, the complete medical image data set is obtained by matching a first, preferably complete image data set, generated at an earlier point in time, as well as possible to a second, incomplete, current image data set, wherein information concerning the surface of the body in the form of a third data set is taken into account. Taking into account the third data set prevents the first image data set from being substantially or at all shifted, rotated or distorted beyond the current surface of the body. Thus, additional information is taken into account when adapting the first image data set. In addition, the information from the first image data set is used rather than the information from the second image data set, even in the region which is captured by the second image data set. This has the advantage that the first image data set, as a CT or MRT image data set, exhibits a greater dynamic range than a second image data set generated by means of a CBCT. The dynamic range of a CBCT is usually significantly lower than that of a CT or MRT, which usually generates values between −1000 and +3000 on the Hounsfield scale.

Furthermore, the complete image data set is not generated by transforming it into a sinogram, supplementing the sinogram and transforming it back into the image region, as in the prior art, but rather directly in the image region. The input of time and the inaccuracies which arise in the course of multiple transformations are thus omitted.

In one embodiment of the invention, the first image data set is adapted to the second image data set by means of elastic image fusion. The principle of elastic image fusion is known to the person skilled in the art of medical imaging. It is based on an iterative process in which the first image data set is modified in steps and the modified image data set is compared with the second image data set. Possible modifications include shifting, rotating or distorting the image data set and can be combined in any way. The surface of the body in the modified first image data set is also referred to as a virtual contour. The comparison between the modified first image data set and the second image data set results in a degree of similarity which represents the similarity between the two image data sets. The modification of the first image data set which results in the greatest degree of similarity results in a first image data set which corresponds as well as possible to the second image data set and thus best represents the current state of the body.

Many different algorithms are known from the prior art, using which elastic image fusion can be implemented and optimized. One option is for example interpolation using thin-plate splines. A thin-plate spline interpolates a surface which is to remain unchanged at predetermined fixed points. This surface represents a thin metal plate which is deformed into the most economic shape in relation to the energy of deformation, i.e. the energy of deformation is minimized. Interpolation by means of thin-plate splines is, as with its derivatives, continuous in its own right, does not have any free parameters which have to be manually set, and features a closed solution.

In elastic image fusion, the third data set is for example taken into account by incorporating the distance between the points of the third data set and corresponding points in the first image data set into the degree of similarity during image fusion. This means that the degree of similarity results not only from the image comparison between the modified first image data set and the second image data set but also from the distance between the surface of the body, which is represented by the third data set, and the surface in the modified first image data set. This prevents the modified first image data set from containing a virtual contour of the body which significantly deviates from the actual contour of the body, wherein it is possible for the distance by which the virtual contour in the modified first image data set exceeds or falls short of the contour of the body represented by the third data set to be incorporated to varying degrees into the degree of similarity. Thus, a distance by which the virtual contour exceeds the actual contour of the body can for example reduce the degree of similarity more significantly than a comparable distance by which the virtual contour falls short of the actual contour.

Alternatively, no modifications of the first data set in which the first region represented by the modified first data set exceeds the contour of the body represented by the third data set are permitted during image fusion. This means that the third data set represents a firm boundary for possible modifications to the first image data set.

In an alternative embodiment, the first image data set is adapted to the second image data set in steps. In a first step, the first image data set is adapted to the second image data set without taking into account the third data set, wherein any adapting method can be used, including for example elastic image fusion. In a second step, the first image data set which was adapted in the first step is segmented, wherein a first segment contains the overlap region between the first region and the second region, and a second segment contains the rest of the first image data set. This means that the first segment represents the region of the body which lies in the detection range of for example the CBCT. All the data outside this region is contained in the second segment.

In a third step, this second segment of the first image data set is adapted by taking into account the third data set. Various methods, for example elastic image fusion, can also be used for adapting here. In this third step, the third data set is preferably taken into account by representing a boundary into which the second segment of the first image data set is fitted, wherein the second segment is preferably adapted such that the transition to the first segment is continuous. This means that the second segment is not changed at the transition area to the first segment.

By adapting the first image data set to the second image data set in steps, the two segments of the first image data set are separately optimized, thus achieving the best possible match between the first image data set and the second image data set in the overlap region between the first region and the second region, while the second segment is modified in accordance with the ancillary conditions provided by the third data set and thus represents the current contour of the body as well as possible.

In the case of elastic image fusion, a deformation field is for example calculated which preferably respectively contains a shift vector for the voxels of the first image data set, in a three-dimensional matrix, wherein a shift vector can be provided for each voxel or only for some of the voxels. When taking into account the third data set, the deformation field is adapted to the contour in the third data set, for example on the basis of corresponding contour control point pairs consisting of a surface point in the first image data set and a corresponding surface point in the third data set. The deformation field is then applied to the first image data set, wherein the data is for example interpolated by means of thin-plate splines. When the present invention is applied to two-dimensional image data, the matrix of the shift vectors is preferably also two-dimensional.

As already explained, the first image data set is preferably ascertained by means of computed tomography (CT) or magnetic resonance tomography (MRT), which generate high-resolution images with a large dynamic range.

The second image data set is preferably ascertained by means of cone beam computed tomography (CBCT). Such an image data set has a lower dynamic range, but can be more quickly generated and with fewer hardware requirements than a CT or MRT data set.

The third data set is for example obtained by laser-scanning the surface or a part of the surface of the body. One possible method for laser-scanning is described in detail in the applicant's European patent application EP 1 142 536 A1, wherein the surface of the body which is to be captured is moved into the detection range of a navigation system which is assisted by at least two cameras and captures the three-dimensional spatial locations of light markings with computer assistance. Light markings are generated on the surface of the body to be referenced by means of a light beam, preferably a tightly focused laser beam, and their three-dimensional location is determined by the camera-assisted navigation system. The location of the light marking is stereoscopically calculated from the locations and alignments of the cameras and from the images generated by them. Optionally, additional information concerning the distance of the light marking from a camera is ascertained from the size of the light marking in the image of the camera. The three-dimensional locations of the scanned surface points are combined to form the third data set. Alternatively, it is possible to project a grid of laser beams onto the surface of the body, capture the grid by means of at least two cameras, and calculate locations of surface points from this, which are stored in the third data set.

Alternatively or additionally, the third data set is obtained by detecting markings on the body. Such a marking can for example be a marker or a marker device.

It is the function of a marker to be detected by a marker detection device (for example, a camera or an ultrasound receiver), such that its spatial position (i.e. its spatial location and/or alignment) can be ascertained. Such markers can be active markers. An active marker emits for example electromagnetic radiation and/or waves, wherein said radiation can be in the infrared, visible and/or ultraviolet spectral range. The marker can also however be passive, i.e. can for example reflect electromagnetic radiation from the infrared, visible and/or ultraviolet spectral range. To this end, the marker can be provided with a surface which has corresponding reflective properties. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can also, however, exhibit a cornered—for example, cubic—shape.

Furthermore, the third data set is alternatively or additionally obtained from x-ray images which contain markings attached on the body. The x-ray images generated by a cone beam computed tomograph when ascertaining the second image data set can for example be used for this purpose. Thus, no additional hardware is necessary in order to obtain the third data set. The markings, preferably in the form of small metal plates or metal spheres, are attached on the body and visible in the individual x-ray images of the CBCT. Another option is to integrate markings, preferably metallic markings, into an item of clothing which lies tightly against the body.

Alternatively, the third data set can also be obtained by scanning the surface of the body by means of a pointer, wherein the tip of the pointer is placed onto various points of the surface of the body and the location of the tip is ascertained.

A pointer is a rod comprising one or more—advantageously, two—markers fastened to it, wherein the pointer can be used to measure off individual coordinates, in particular spatial coordinates (i.e. three-dimensional coordinates), on a body, wherein a user guides the pointer (in particular, a part of the pointer which has a defined and advantageously fixed position with respect to the at least one marker which is attached to the pointer) to the location corresponding to the coordinates, such that the location of the pointer can be determined by using a surgical navigation system to detect the marker on the pointer. The relative position between the markers of the pointer and the part of the pointer used to measure off coordinates (in particular, the tip of the pointer) is in particular known. The surgical navigation system then enables the location (the three-dimensional coordinates) of the part of the pointer contacting the body and therefore the contacted point on the surface of the body to be calculated, wherein the calculation can be made automatically and/or by user intervention.

The present invention also relates to a computer program which, when it is run on a computational unit, performs one or more of the method steps described above.

Within the framework of the invention, computer program elements can be embodied by hardware and/or software (this also includes firmware, resident software, micro-code, etc.). Within the framework of the invention, computer program elements can take the form of a computer program product which can be embodied by a computer-usable or computer-readable storage medium comprising computer-usable or computer-readable program instructions, "code" or a "computer program" embodied in said medium for use on or in connection with the instruction executing system. Such a system can be a computer; a computer can be a data processing device comprising means for executing the computer program elements and/or the program in accordance with the invention. Within the context of this invention, a computer-usable or computer-readable medium can be any medium which can contain, store, communicate, propagate or transport the program for use on or in connection with the instruction executing system, apparatus or device. The computer-usable or computer-readable medium can for example be, but is not limited to, an electronic, magnetic, optical, electromagnetic, infrared or semiconductor system, apparatus, device or medium of propagation, such as for example the Internet. The computer-usable or computer-readable medium could even for example be paper or another suitable medium onto which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiment(s).

The method in accordance with the invention is in particular a data processing method. The data processing method is preferably performed using technical means, in particular a computer. The computer in particular comprises a processor and in particular a memory in order to process the data, in particular electronically. The calculating, adapting or comparing steps described are in particular performed by a computer. Steps of defining for example regions or values are in particular steps of determining data within the framework of the technical data processing method, in particular within the framework of a program. Steps of modifying in particular represent changing the data by means of the computer. Steps of ascertaining in particular include retrieving values which are provided at an interface of the computer and have been generated by technical means, such as for example a scanning device. These values are in particular converted by the interface into data which can be processed by the computer.

The present invention also comprises a device for generating a complete image data set from an incomplete image data set. The device comprises an interface for receiving a first image data set which represents an image of a first region of a body, including a part of the surface of the body, at a first point in time. The device can for example be connected via the interface to a medical image forming device for a computed tomograph or a magnetic resonance tomograph. Alternatively, the device can be connected via the interface to a memory in which the first image data set is stored. This memory can also be part of the device.

The device also comprises a device for generating a second, incomplete image data set which represents an image of a second region of the body at a second point in time, wherein the first region and the second region overlap. This device is preferably a cone beam computed tomograph.

The device also comprises a device for generating a third data set which represents the contour of the body, substantially at the second point in time. This device is for example a laser-scanning device such as has already been described above.

The device also comprises a computational unit which is configured to adapt the first image data set to the second image data set by taking into account the third data set and to accept the adapted first image data set as a complete image data set.

Optionally, other components are provided in the device, or available components such as the computational unit are designed such that they are suited to performing one or more of the aforesaid method steps.

In one embodiment of the invention, the device also comprises a radiotherapy device which for example contains a LINAC (linear accelerator) and can be controlled on the basis of the complete image data set. A treatment plan can be derived from the complete image data set, on the basis of which the radiotherapy device is configured and activated.

The therapy beam generated by the radiotherapy device can optionally be used for imaging, i.e. in particular for generating the second image data set. The therapy beam usually exhibits a higher energy level than an x-ray beam, for example in the megavolt (MV) range as compared to the kilovolt (kV) range in the case of x-ray radiation. Image data obtained by means of the therapy beam is therefore also referred to as an MV CBCT. The MV CBCT projection images, alone or in combination with the kV CBCT projection images of an x-ray device, can be used to reconstruct three-dimensional image data.

Preferably, at least the device for generating the second image data set is arranged on a support, which is also referred to as a gantry, wherein the support can be rotationally and/or translationally moved, for example with respect to a table on which the body is situated. Other devices, such as the device for generating a third data set or the radiotherapy device, or components of the devices are optionally arranged on the same support. The position of the devices and/or components relative to each other and thus known, and the position of the devices and/or components with respect to the body can be changed by moving a single support.

BRIEF DESCRIPTION OF THE DRAWINGS

The present invention shall be explained in more detail on the basis of an example embodiment.

DETAILED DESCRIPTION

Figure 1:
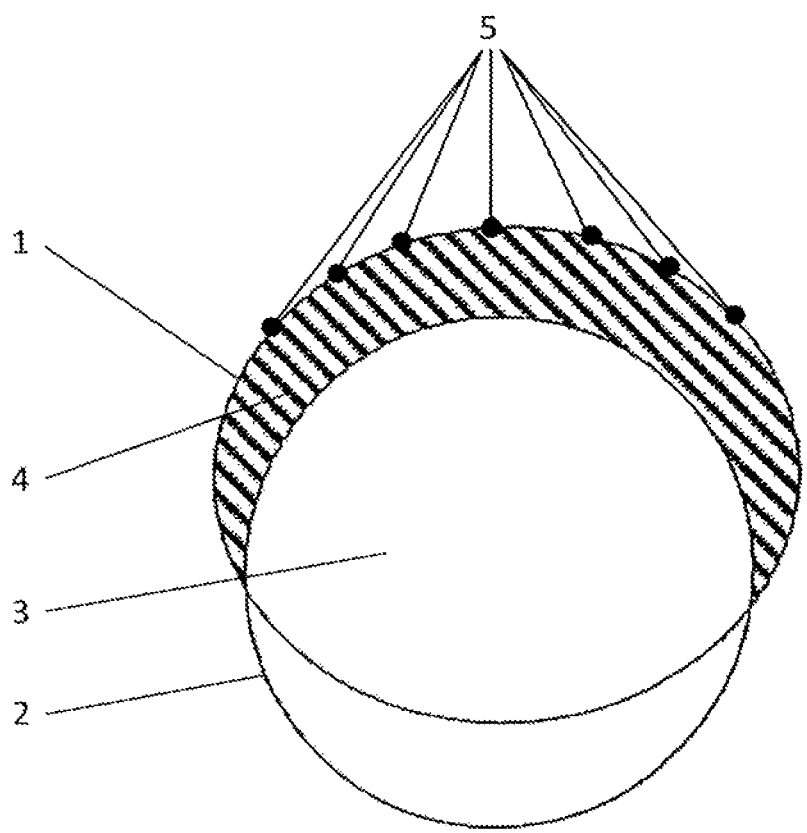
FIG. 1 shows the contour of a body, the detection range of a CBCT and some surface points.

FIG. 1 schematically shows a cross-section through a body 1, the surface of which exhibits an elliptical shape in the present example embodiment. Some points 5 on the surface of the body 1 are symbolized by circles. FIG. 1 also shows a detection range 2 of the cone beam computed tomograph. The body 1 and the detection range 2 overlap in an overlap region 3. The region 4 of the body 1, represented by cross-hatching, is not covered by the detection range 2.

For reasons of representation, FIG. 1 shows the body 1 and the regions 2, 3 and 4 two-dimensionally. In practice, however, they are predominantly three-dimensional. The detection range 2 is for example spherical.

Figure 2:
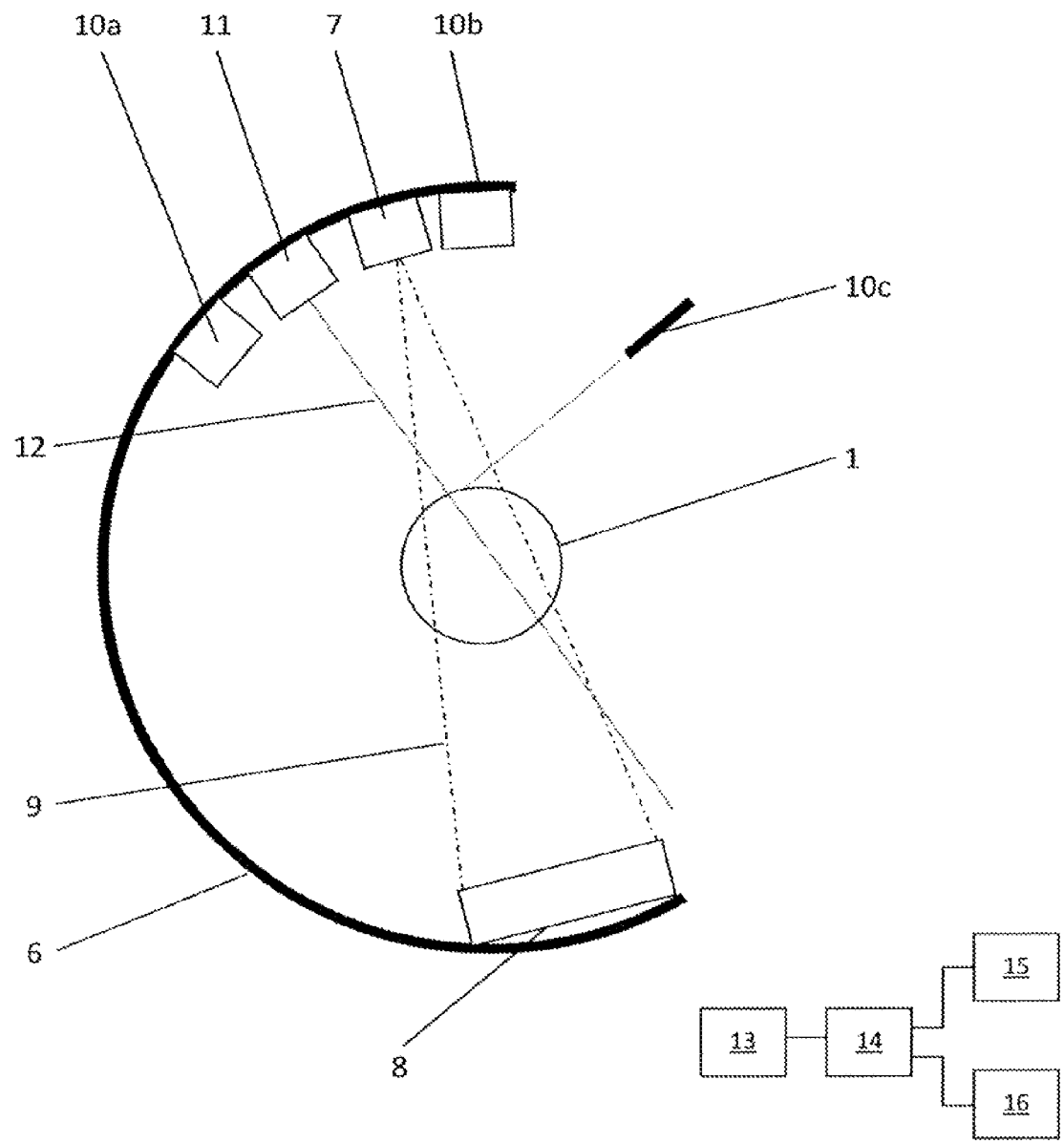
FIG. 2 shows the device in accordance with the invention.

FIG. 2 shows a device in accordance with the invention which is for example based on a C-shaped or circular arc-shaped support 6. However, any other suitable construction can be provided as the support for the individual components of the device—for example, an x-ray device in the form of a so-called C-arm, which is supplemented by additional devices.

An x-ray source 7 and an x-ray detector 8 are arranged on the support 6 in such a way that the conical x-ray beam 9 of the x-ray source 7 is irradiated through the body 1 and hits the x-ray detector 8. By rotating the support 6 about its rotational axis—which in the present example is perpendicular to the plane of the drawing—it is possible to generate x-ray recordings of the body 1 from various viewing directions and to calculate them into a three-dimensional image.

The two cameras 10a and 10b are also arranged on the support 6. Instead of on the support 6, these cameras can also be arranged stationary with respect to the body 1, for example on a stand or on a ceiling or wall of a room. A laser beam is generated by means of a laser generator 10c and can be directed onto the body 1. The cameras 10a and 10b capture the light mark generated by the laser generator 10c on the surface of the body 1. The spatial location of the light mark, and therefore the location of the illuminated point on the surface of the body 1, can be determined on the images of the cameras 10a and 10b.

An optional beam generator 11, which is also referred to as a linear accelerator (LINAC), is also arranged on the support 6. It serves to generate a treatment beam 12 which is for example suitable for irradiating a tumor in the body 1. The beam generator 11 is part of a radiotherapy device.

In order to correctly plan the use of the radiotherapy device, but also for a multitude of other medical applications, it is necessary to have an image of the body 1 immediately before the irradiation and/or treatment. Such an image can be generated by means of a cone beam computed tomograph which contains the x-ray source 7 and the detector 8. However, as can be seen from FIG. 1, the detection range 2 of the CBCT often does not include the entire body 1. It is therefore necessary to supplement the incomplete image data set generated by the CBCT, to form a complete medical image data set.

To this end, a first image data set is initially provided which represents an image of a first region of a body 1, including at least a part of the surface of the body, at a first point in time. In the present example, the first region—as viewed in cross-section—includes the complete body 1. A second, incomplete image data set is also provided which represents an image of a second region 2 of the body 1 at a second point in time, wherein the first region and the second region 2 overlap. A third data set is also provided which represents the contour of the body 1 in the form of points 5 on the surface of the body 1, substantially at the second point in time. The second point in time is for example immediately before the treatment and/or irradiation of the body 1. The second image data set is ascertained by means of the x-ray source 7 and the x-ray detector 8 of a cone beam computed tomograph. The third data set is ascertained by illuminating points 5 on the surface of the body 1 by means of the laser beam of the laser source 10c, and the reflection of the laser beam on the surface of the body 1 is captured by the cameras 10a and 10b. The location of the reflection point and therefore of the surface point 5 can be calculated from the images generated by the cameras 10a and 10b and from the spatial arrangement of the cameras with respect to each other. The second image data set and the third data set preferably relate to a common coordinate system which is for example defined in relation to the body 1 or to the support 6.

The first image data set is generated by means of a fan beam computed tomograph (CT) or a magnetic resonance tomograph (MRT). The first point in time, at which the first image data set is generated, can be minutes or hours or also days or even weeks before the second point in time.

The third data set is generated at substantially the point in time at which the second image data set is generated, i.e. at the second point in time. This means that the time of generating the third data set and the time of generating the second image data set are closer together than the first point in time and the second point in time. The second image data set and the third data set are preferably recorded simultaneously or at least in immediate succession.

In the subsequent progression of the method, the first image data set is adapted to the second image data set by taking into account the third data set. This means that the first image data set is modified such that it corresponds as well as possible to the second image data set, wherein the third data set defines an ancillary condition for the modification. The adapted first image data set is then accepted as a complete image data set. This means that the second image data set is not accepted into the complete image data set, but rather merely serves as a reference for adapting the first image data set, such that the first image data set represents as well as possible the state of the body 1 at the second point in time.

In the present example embodiment, the first image data set is adapted by means of elastic image fusion, wherein a multitude of modified image data sets are iteratively generated by shifting, rotating or distorting the first image data set, wherein any combination of these modifications is also possible. Each modified image data set is compared with the second image data set, resulting in a degree of similarity, which represents the similarity between the two image data sets, for each image comparison.

Two variants of adapting are described in the following. In the first variant, a distance value is incorporated into the degree of similarity of elastic image fusion, in addition to the similarity between the modified first image data set and the second image data set. This distance value is determined from the distance between the points 5, which are represented by the third data set, and the surface of the body 1 in the modified first image data set. Modifying the first image data set results in a new, virtual profile of the surface of the body 1 in the modified first image data set. This modified first surface (or virtual contour) is compared with the contour of the body, as stored in the third data set on the basis of the points 5. The greater the distance between the modified surface in the modified first image data set and the surface in the third data set, the more significantly the degree of similarity resulting from the comparison between the modified first image data set and the second image data set is reduced. This can reach the point where the degree of similarity is reduced to zero, if some or all of the points 5 in the modified first image data set lie within the body 1, i.e. the virtual contour of the body 1 in the modified first image data set extends beyond the measured surface of the body 1 represented by the third data set, at the second point in time. In this case, the third data set serves as a firm boundary for possible modifications to the first image data set during elastic image fusion.

The distance value is for example the sum of the distances between the individual points 5 and the virtual contour in the modified first image data set or its average value. The distance is for example the minimum distance between a point 5 and the virtual contour or the distance from a corresponding point, for example a landmark. A landmark is a defined, characteristic point of an anatomical structure which is always identical or recurs with a high degree of similarity in the same anatomical structure of a number of patients. Typical landmarks are for example the epicondyles of a femoral bone, the tips of the transverse processes and/or dorsal process of a vertebra or points such as the tip of the nose or the end of the root of the nose.

In accordance with a second variant, the first image data set is adapted to the second image data set in steps. In a first step, the first image data set is adapted to the second image data set, for example by means of elastic image fusion, without taking into account the third data set. The result of this is that the adapted first image data set and the second image data set are optimally matched in the overlap region 3 after the first step. The first image data set which was adapted in the first step is then segmented, such that the first segment represents the overlap region 3 and a second segment contains the rest of the adapted first image data set. In a third adapting step, the second segment of the first image data set is adapted in the region 4 to be supplemented. The second segment of the first image data set is for example adapted such that it is optimally fitted into the region 4 which is limited on the one hand by the boundary of the first segment of the modified first image data set and on the other hand by the points 5 in the third data set. In this step, it is possible to take into account the ancillary condition that the transition from the first segment to the second segment of the first image data set should run continuously, i.e. the data of the second segment which immediately borders the first segment is not changed or only slightly changed.

The advantage of the second variant is that the first image data set is optimally matched to the second image data set in the detection range 2 of the CBCT, while the first image data set is simultaneously optimally fitted into the contour of the body 1 represented by the third data set.

The device also comprises a computational unit 13 which is connected to the x-ray generator 7 and the x-ray detector 8. The computational unit 13 activates the x-ray generator 7 and receives the output signals of the x-ray detector 8. The computational unit 13 is also configured to move the support 6 into various locations in relation to the body 1. The computational unit 13 calculates a three-dimensional image of the body 1—which is stored in a second image data set—from the output signals of the x-ray detector 8 in the various locations of the support 6. The computational unit 13 is connected via an interface 14 to a computed tomograph 15 or a memory 16. The first image data set is for example generated by the computed tomograph 15 and provided to the computational unit 13 via the interface 14. Alternatively, the first image data set is stored in the memory 16 and provided to the computational unit 13 via the interface 14. For reasons of clarity, the connections between the computational unit 13 and the components arranged on the support 6 are not shown in FIG. 2.

Optionally, the computational unit 13 is also connected to the cameras 10a and 10b, such that it can calculate the location of the points 5 from the output signals of the cameras 10a and 10b and their position. Alternatively, the computational unit 13 is connected via the interface 14 or an interface which is not shown to a second computational unit which is in turn connected to the cameras 10a and 10b and calculates the location of the points 5 from their output signals and position, and provides it to the computational unit 13.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, "code" or a "computer program" embodied in said medium for use by or in connection with the instruction executing system. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electro-magnetic, infrared or semiconductor system, apparatus, device or medium of propagation, such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiment(s).

Although the invention has been shown and described with respect to one or more particular preferred embodiments, it is clear that equivalent amendments or modifications will occur to the person skilled in the art when reading and interpreting the text and enclosed drawing(s) of this specification. In particular with regard to the various functions performed by the elements (components, assemblies, devices, compositions, etc.) described above, the terms used to describe such elements (including any reference to a "means") are intended, unless expressly indicated otherwise, to correspond to any element which performs the specified function of the element described, i.e. which is functionally equivalent to it, even if it is not structurally equivalent to the disclosed structure which performs the function in the example embodiment(s) illustrated here. Moreover, while a particular feature of the invention may have been described above with respect to only one or some of the embodiments illustrated, such a feature may also be combined with one or more other features of the other embodiments, in any way such as may be desirable or advantageous for any given application of the invention.

What is claimed is:

1. A data processing method, performed by a computer for generating a complete medical image data set from an incomplete image data set, comprising:
    providing a first image data set which represents an image of a first region of a body, including at least a part of the surface of the body, at a first point in time;
    providing a second image data set which represents an image of a second region of the body at a second point in time, wherein the second image data set has less dynamic range than the first image data set and/or the second image data set represents only a portion of the first region; and the first region and the second region at least partially overlap;
    providing a third data set which represents a boundary of the body in the form of points on the surface of the body over the second region, substantially at the second point in time;
    using the computer to adapt the first image data set to the second image data set by incorporating a distance between points of the third data set and corresponding points in the first image data set; and
    accepting the adapted first image data set as a complete image data set.

2. The method according to claim 1, wherein the first image data set is adapted by means of elastic image fusion.

3. The method according to claim 2, wherein the third data set is taken into account by incorporating the distance between the points of the third data set and corresponding points in the first image data set into the degree of similarity during image fusion.

4. The method according to claim 3, wherein no modifications of the first data set in which the first region represented by the first data set exceeds the boundary of the body represented by the third data set are permitted during image fusion.

5. The method according to claim 1, wherein the first image data set is modified in steps, wherein:
    in a first step, the first image data set is adapted to the second image data set without taking into account the third data set;
    in a second step, the first image data set which was adapted in the first step is segmented, wherein a first segment contains the overlap region between the first region and the second region, and a second segment contains the rest of the first image data set; and
    in a third step, the second segment of the first image data set is adapted by taking into account the third data set.

6. The method according to claim 1, wherein the first image data set is ascertained by means of computed tomography or magnetic resonance tomography.

7. The method according to claim 1, wherein the second image data set is ascertained by means of cone beam computed tomography.

8. The method according to claim 1, wherein the third data set is obtained by laser-scanning the body.

9. The method according to claim 1, wherein the third data set is obtained by detecting markings on the body.

10. The method according to claim 1, wherein the third data set is obtained from x-ray images which contain markings attached onto the body.

11. A computer program embodied on a non-transitory computer-readable medium comprising computer executable instructions adapted to perform the steps of:
    providing a first image data set which represents an image of a first region of a body, including at least a part of the surface of the body, at a first point in time;
    providing a second image data set which represents an image of a second region of the body at a second point in time, wherein the second image data set has less dynamic range than the first image data set and/or the second image data set represents only a portion of the first region; and the first region and the second region at least partially overlap;
    providing a third data set which represents a boundary of the body in the form of points on the surface of the body over the second region, substantially at the second point in time;
    adapting the first image data set to the second image data set by incorporating a distance between points of the third data set and corresponding points in the first image data set; and accepting the adapted first image data set as a complete image data set.

12. A device for generating a complete medical image data set from an incomplete image data set, comprising:
- an interface for receiving a first image data set which represents an image of a first region of a body, including at least a part of the surface of the body, at a first point in time;
- a device for generating a second image data set which represents an image of a second region of the body at a second point in time, wherein the second image data set has less dynamic range than the first image data set and/or the second image data set represents only a portion of the first region; and the first region and the second region at least partially overlap;
- a device for generating a third data set which represents a boundary of the body in the form of points on the surface of the body, substantially at the second point in time; and
- a computational unit which is configured to adapt the first image data set to the second image data set by incorporating a distance between points of the third data set and corresponding points in the first image data, and to accept the adapted first image data set as a complete image data set.

13. The device according to claim 12, wherein the device for generating the second image data set is a cone beam computed tomograph.

14. The device according to claim 12, wherein the device for generating the third image data set is a laser scanning device.

15. The device according to claim 12, comprising a radiotherapy device which can be controlled on the basis of the complete image data set.

* * * * *